United States Patent [19]

Lux

[11] 4,241,404
[45] Dec. 23, 1980

[54] DEVICE FOR COMPUTED TOMOGRAPHY

[75] Inventor: Peter Lux, Hamburg, Fed. Rep. of Germany

[73] Assignee: U.S. Philips Corporation, New York, N.Y.

[21] Appl. No.: 970,596

[22] Filed: Dec. 18, 1978

[30] Foreign Application Priority Data

Dec. 19, 1977 [DE] Fed. Rep. of Germany ....... 2756659

[51] Int. Cl.$^3$ ............................................ G01N 21/00
[52] U.S. Cl. ................................ 364/414; 250/445 T
[58] Field of Search ................ 250/445 T, 360, 363 S; 364/414; 358/111

[56] References Cited

U.S. PATENT DOCUMENTS

| | | | |
|---|---|---|---|
| 4,032,761 | 6/1977 | Mayo et al. | 364/414 |
| 4,064,393 | 12/1977 | Pasedach et al. | 364/414 |
| 4,101,768 | 7/1978 | Lill | 250/445 T |
| 4,143,273 | 3/1979 | Richey et al. | 250/445 T |
| 4,144,570 | 3/1979 | Wagner | 364/414 |
| 4,168,436 | 9/1979 | Aradate et al. | 250/445 T |

*Primary Examiner*—Errol A. Krass

*Attorney, Agent, or Firm*—Thomas A. Briody; Robert T. Mayer; Jack E. Haken

[57] ABSTRACT

For determining the absorption distribution in a plane of a body by means of a fan of radiation beams from an approximately point-shaped radiation source and in different positions of the body with respect to the radiation source, a detector element comprising only one amplifier is used for a number of adjacent radiation beams or all radiation beams. For determining the intensity profile in each measuring position, the radiation beams are modulated by time functions which form a complete, linearly independent function system (Walsh functions). Modulation is realized by means of an aperture which is constructed as a rotating disc which comprises transmissive and non-transmissive sectors. At each change of a function value, a discrete signal value is derived from the detector signals, so that the total number of signal values equals the number of functions of the function system. The signal values are multiplied by a back transformation matrix and therefrom the intensity profile is recovered. This profile is processed in known manner in order to obtain an absorption image. This principles is also suitable for a two-dimensional fan of radiation beams for the simultaneous determination of the absorption distribution in a plurality of planes.

19 Claims, 6 Drawing Figures

DEVICE FOR COMPUTED TOMOGRAPHY

The invention relates to a device for determining the absorption distributions of a body by means of a substantially point-shaped source for generating radiation which penetrates the body, a detector device for measuring the radiation having passed through the body and for generating a detector signal, and a processing device for deriving from the detector signals electrical signals which represent the absorption of the body along neighbouring radiation beams.

A device of this kind, which is used notably in the medical X-ray technique is known, for example, from German Offenlegungsschrift No. 24 39 847. The radiation generated by the radiation source is stopped to form a fan-shaped radiation beam which is directed onto the body and which is incident on a detector device which is arranged at the opposite side of the body and which consists of a detector element for measuring radiation along each radiation path. Each detector element consists of a scintillation crystal, and a photomultiplier and an amplifier connected thereto. The gain of the amplifiers must be individually adjusted to the sensitivity of the crystals and of the photomultipliers. The chain formed by the crystal, the photomultiplier and the amplifier must provide an as accurately as possible equal conversion of the radiation into an electrical signal for all detector elements in order to allow reproducible results to be obtained. This requires a very careful (and hence expensive) adjustment of the individual amplifiers which, moreover, must be repeated at regular intervals due to the aging of the various elements, Apart from the very high manufacturing costs in the form of a large number of photomultipliers and amplifiers, the known device also implies high operating costs due to the continuously required supervision and adjustment by expert personnel.

The invention has for its object to provide a device whereby the absorption distribution can be measured with lower manufacturing and as operating costs.

To this end, a device in accordance with the invention is characterized in that the detector device comprises only one detector element for a group of adjacently situated radiation beams, a modulation device, which modulates the intensity of the radiation beams according to time functions which form a, linearly independent function system for the radiation beams detected by a detector element. Each function is unambiguously assigned to a radiation beam. The functions contain only positive function values. The processing device derives from the detector signals a number of discrete signal values which are preferably situated at approximately the same distance from each other in time and stores said signal values. The number of discrete signal values is equal to the number of functions in the associated function system. The processing device produces the signal values, which are representative of the absorption, by multiplication of the discrete signal values by a matrix of values which is inverted with respect to the matrix of values of the function values of the functions used during modulation in the locations corresponding to the taking up of the discrete signal values, and by subsequently taking the logarithm of the products. Thus, only one scintillation crystal or a composite crystal, only one photomultiplier and only one amplifier are required for a number of radiation beams. A change of the sensitivity, that is to say a change of the characteristic of the electrical signal as a function of the radiation, uniformly affects a larger number of parallel radiation beams, so that there are no incorrect measurements due to changes in the sensitivity of the detector and hence no changes of the measuring signals with respect to each other; rather all signals are uniformly influenced should the intensity of the radiation source change. This is applicable to all kinds of detector elements. A change during a measurement is distributed more or less among all electrical signals, depending on the modulation function system used, so that it becomes manifest only in the case of a substantially reduced amplitude.

The discrete signal values derived from the detector signals by the processing device should correspond to given function values of the functions used during modulation, i.e. they should represent instantaneous values. However, for various reasons such instantaneous values are incorrect, for example, due to the strong noise which occurs for the low radiation doses used in the field of medical applications. Therefore, it is advantageous for the modulation device to modulate each radiation beam with discrete function values of the associated functions during a predetermined period of time, the number of discrete function values being equal to the number in functions used of the relevant function system. The function values are derived at approximately equal time intervals from the functions in accordance with the locations where the discrete signal values are in the processing device. During the period of modulation by a discrete function value, the electrical signal supplied by the detector device is integrated, with the result that the effect of quantum noise is substantially reduced, the discrete signal value being derived by the processing device only at the end of the modulation period. Between the individual modulation periods, intervals can be introduced during which the overall radiation intensity is zero.

The absorption values of the adjacent radiation beams from an absorption function with sequence 5 of a different order up to the maximum number of radiation beams detected by the detector element. It has been found that the visual image impression is not influenced when the higher sequence in this absorption function contain more noise than the lower sequences. In order to reduce the overall dose during the irradiation of the body, it is advantageous for the modulation device to modulate the radiation beams by the associated function values of those functions which produce the higher sequences of the absorption function formed by the series of absorption values of the adjacent radiation beams for a shorter period of time than the radiation beams by the function values of the other functions and to block these radiation beams completely during the residual period. When an interval is inserted between successive function values during the modulation by discrete function values. The interval is extended accordingly for the functions for the higher sequences.

Another possibility of reducing the radiation dose used during the examination of the body is that the function is omitted which supplies an equivalent value from the function systems, i.e. the mean value of the absorption values for the radiation beams of a detector element. This is because the equivalent value is eliminated anyway by the filtering process during the reconstruction of the two-dimensional absorption distribution. A fictitious equivalent value can then be used for the multiplication of the discrete signal values by the matrix of function values. The value is chosen to be large enough so that no negative values are formed during the multiplication.

It has been found that preferably only one detector element is provided for all radiation beams. In that case, only one amplifier, which can be easily adjusted is required. The gain drift thereof which occurs in the course of time only changes the overall image brightness.

Only a fan-shaped radiation beam in one dimension was considered thus far. When several parallel layers are to be examined, the absorption values of the individual layers are generally consecutively determined. In an embodiment in accordance with the invention, however, it is advantageous for the radiation beams to form a two-dimensional fan for each layer. A detector element is provided for the radiation beams which are adjacent in one dimension (in this layer). When a detector element is present for all radiation beams in a plane, a detector element is required for each layer. The radiation beams adjacently extending in the various layers are then modulated by the same functions, and the processing device treats the electrical signals of the individual detector elements in the same way.

In the case of a two-dimensional fan it is also advantageous to provide only one detector element for all radiation beams. The modulation device modulates the radiation beams in accordance with time functions which form a two-dimensional, complete, linearly-independent function system. In that case, the processing device must multiply the discrete signal values by a three-dimensional matrix or it must perform a two-sided multiplication by two-dimensional matrices in order to determine a two-dimensional matrix of absorption signals.

Various complete, linearly-independent function systems are known, for example, the system of sine and cosine functions used for the Fourier analysis. The use of such a function system, however, requires modulation by a large number of different values, which may be problematic. Therefore, it is particularly useful if the function system is the Walsh-Hadamard functions. For these functions, only the value 1 or 0 is used for the modulation in accordance with the invention, which means that a radiation beam is completely transmitted or completely blocked, which is readily possible. Other function systems which can assume only two different values are the Haar functions such as the m-functions described in the magazine "Frequenz", Vol. 7 (1976), pp. 196 to 199.

Preferably, the modulation device consists of an aperture which is mechanically moved between the radiation source and the detector device and which comprises radiation-transmissive zones and non-transmissive zones in accordance with the functions of the function system. A modulation device of this kind can be used for the various kinds of radiation sources, notably also for X-radiation. The aperture effectively consists of one or more rotating discs. Modulation with a comparatively high frequency can also be readily obtained by means of such an aperture construction.

The discrete signal values derived from the detector signals by means of the processing device should correspond as accurately as possible to given function values or to given instants during the modulation by discrete function values. Therefore, synchronization signals for controlling the taking up of the discrete signal values by the processing device are preferably derived from the movement of the aperture. Thus, a necessary relationship between the derived signal values and given function values at given instants is ensured.

Embodiments in accordance with the invention will be described in detail hereinafter with reference to the accompanying diagrammatic drawing.

Figure 1:
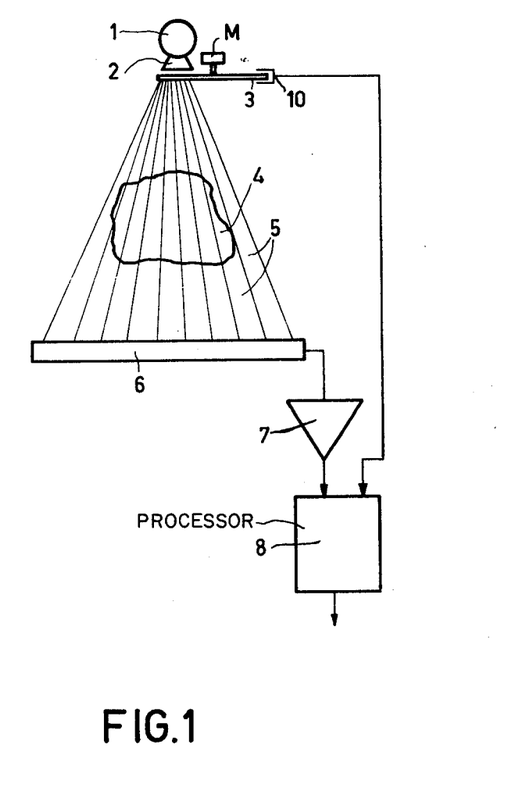
FIG. 1 is a diagrammatic view of a device in accordance with the invention.

A mainly point-shaped source 1 in FIG. 1 supplies the radiation for examining the body 4. This source 1 may be, for example, an X-ray tube. In front of this source 1 there is arranged a collimator 2 which stops the radiation generated to form a fan of radiation beams 5 which is situated in the plane of the drawing.

In front of the collimator 2 there is arranged an aperture 3 in the form of a rotating disc which is driven by a motor M. This aperture 3 modulates the individual radiation beams according to different time functions.

The radiation beams 5 reach the body 4 to be examined and are attenuated according to the integral of the absorption of the body along the radiation beam during the passage through this body. The radiation emerging from the body 4 reaches a detector device 6 which in this case consists of a single detector element. This detector element 6 may consist of one or more scintillation crystals, light flashes from which are detected by a single photomultiplier, or of a xenon measuring chamber, and supplies an electrical signal which corresponds to the total radiation incident on the detector 6. The electrical detector signal is amplified in an amplifier 7 whose gain is set for a given conversion of radiation into electrical signals, so that a standardized signal is applied to the actual processing device 8. From this signal, the processing device 8 derives, by means of the synchronization signal derived from the movement of the aperture 3 by a position detector 10, a succession of signals which correspond to the absorption of the body 4 along the individual radiation beams 5 in the sequence of their position shown in the drawing.

Figure 2:
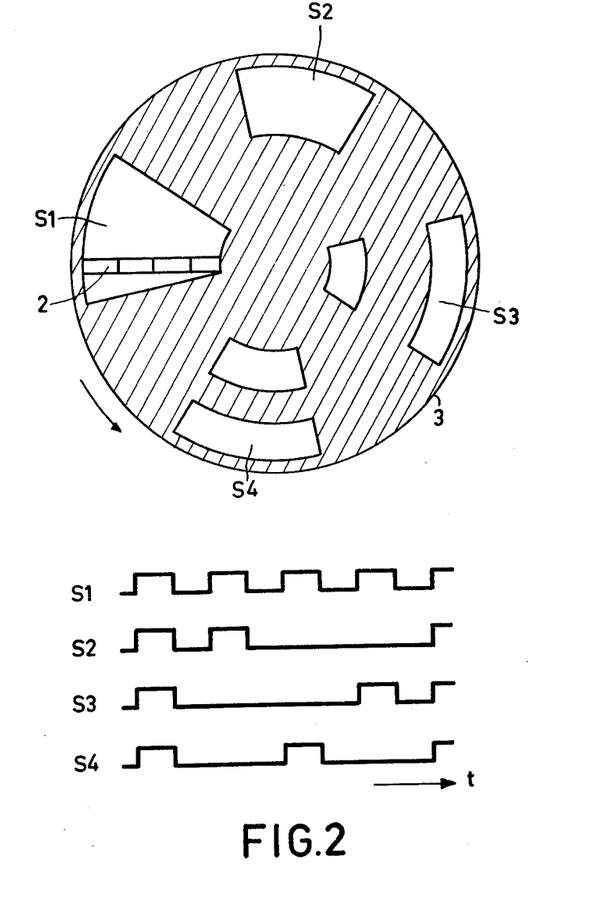
FIG. 2 shows an embodiment of a disc-shaped aperture, utilizing the Walsh-Hadamard functions in accordance with the invention.

For the description of the operation of this device, it is assumed that the aperture 3 modulates the individual radiation beams in accordance with Walsh-functions. FIG. 2 shows a rotating aperture which is suitable for this purpose. This aperture comprises four sectors S1 to S4, comprising passages which can transmit the radiation, while the shaded areas cannot transmit radiation. The four sectors are separated from each other by sections which are not transmissive. In the position of the aperture 3 shown, the collimator 2 arranged in front of the radiation source is situated exactly behind the sector S1. FIG. 2 shows a subdivision of the collimator into four sections; however, the collimator can actually comprise many more sections, for example, from 100 to 200. The four adjoining sections represent radiation beams. During rotation in the direction of the arrow, the four radiation beams are modulated in time as shown in the time diagram of FIG. 2. By removal of the parts of the four curves in this diagram which are generated by the non-transmissive zones between the sectors of the aperture, exactly those 4 first Walsh functions are obtained whose values correspond to the Hadamard matrix of the fourth order:

$$[H_4] = \begin{matrix} 1 & 1 & 1 & 1 \\ 1 & 1 & -1 & -1 \\ 1 & -1 & -1 & 1 \\ 1 & -1 & 1 & -1 \end{matrix}$$

For this comparison it is assumed of course that the function values $-1$ are replaced by the value 0 during the modulation, because negative radiation actually does not exist. The functions $M_i(x)$ used for modulating, x assuming the value 0 or 1 and indicating the annular displacement of the aperture during a revolution and hence the time, are thus derived from the Walsh functions as follows:

$$M_i(x)_0{}^1 = \tfrac{1}{2}[Wal(i,x) + Wal(0,x)]$$

If the output signal of the detector element 6 or of the amplifier 7 is integrated during the period during which each time a sector of the aperture is situated in front of the collimator 2 and is sampled at the end of this period, these signals represent the spectral values $F'_w(i)$ modified due to the modulation by shifted Walsh functions which are related to the spectral Walsh values as follows:

$$F'_w(i)_0{}^1 = \tfrac{1}{2}[F_w(i) + F_w(0)].$$

The non-modified spectral Walsh values $F_w(i)$ then have the following result:

$$F_w(i) = 2F'_w(i)_0{}^1 - F_w(0)_0{}^1.$$

In these equations, the letter i denotes the sequence number of the radiation beams, i.e. starting with 0 from the left in the diagram shown in FIG. 2. From the non-modified spectral Walsh values thus obtained, the function of the spatial distribution of the radiation intensity on the detector element can be determined, in that these spectral values are multiplied by a matrix which is inverted with respect to the matrix used during the modulation. In the case of the Walsh-Hadamard functions, this is the same, already described Hadamard matrix of the fourth order. From the intensity distribution thus obtained, the absorption distribution that is to say the integral of the absorption of the body along the individual radiation beams can be determined in known manner by logarithmation, that is to say the integral of the absorption of the body along the individual radiation beams.

Hereinafter, this process will be described on the basis of a numerical example for which it is assumed that the body has an absorption distribution such that the radiation beams transmitted by the aperture reach the detector element with the following intensities, taken from left to right (shown relatively in this case): 1; 2; 3; 4. During the rotation of the aperture, starting with the sector S1, the detector time then successively supplies signals in accordance with the following total intensities: 10; 3; 5; 4. In order to obtain from these modified spectral values the original spectral values of the spatial intensity distribution of the radiation from all radiation beams incident on the detector, the latter equation is used and the following values are obtained; 10; $-4$; 0; $-2$. If these spectral values as a matrix of one column are mutliplied by the Hadamard matrix of the fourth order, the following values are obtained: 4; 8; 12; 16. With the exception of the standardization factor 4, these are the intensities of the radiation beams when they reach the detector element, i.e. in the same sequence.

The number of four radiation beams is merely chosen for the sake of clarity in the described example. Obviously, a much higher resolution is required in practice, necessitating a much larger number of radiation beams and hence a much larger number of functions used. The system of the Walsh functions is defined up to arbitrarily high orders. The aperture 3 then comprises a correspondingly larger number of sectors, i.e. equal to the number of different radiation beams, and the sectors are then more finely subdivided in accordance with the Walsh functions.

In the Walsh functions, the discrete function values are equal the function values for a given section at given instants, and these discrete function values can also assume only two different numerical values, so that the formation of the aperture is particularly simple in this case. In principle, however, other complete, linearly-independent function systems can also be used which contain, for example, continuous functions. When use is made of an aperture for the modulation by the overall function variation of such continuous functions, this aperture can comprise, at the separations between each time two radiation beams, a bridge whose width on either side of the radiation beam corresponds to the function used. The separating zones between the sectors can then be complete omitted, as for the described Walsh functions, if so permitted by the stability of the aperture. The aperture may alternatively be constructed as a filter which comprises regions of different transmissivity in accordance with the functions used.

The described aperture with the Walsh-Hadamard functions must be rotated for each relative angular position of the body with respect to the device 1–6 so that all values of all functions pass the collimator 2 exactly once, which implies one revolution when these functions are distributed over the total circumference of the aperture.

Figure 3:
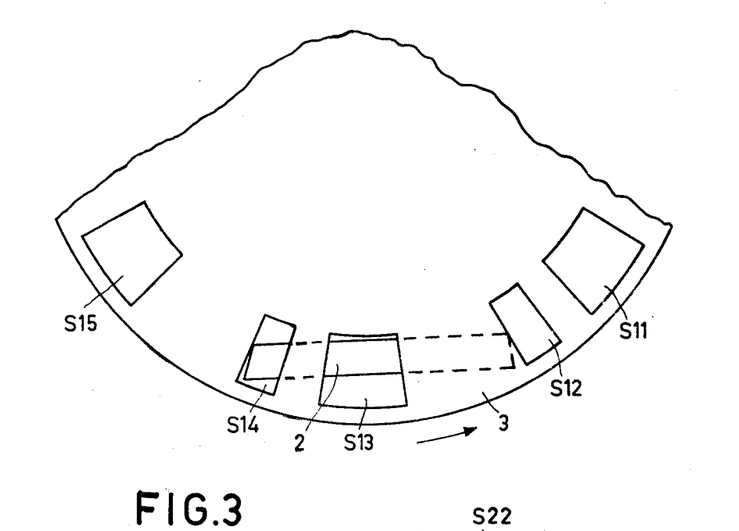
FIG. 3 shows a further embodiment of an aperture, utilizing the m-functions in accordance with the invention.

A suitable aperture for use for the modulation by m functions is shown in FIG. 3. This aperture again consists of a rotating disc, the individual function values of the various functions which are simultaneously used during the modulation of the beams no longer being radially arranged but rather being distributed over the circumference. As appears from said article in "Frequenz", Vol. 7, (1967) pp. 196–199, each function arises from the preceding function in that it is cyclically shifted over a sub-interval. Different series of the same function are successively provided on the disc; each function comprising two transmitting sectors. This means that a function may extend from the beginning of the sector S11 up to and including the beginning of the sector S13 and may also cover the sector S12. The adjoining and same function extends from the beginning of the sector S13 up to and including the beginning of the sector S15 and also covers the sector S14, etc. FIG. 3 only shows a part of the aperture 3 which illustrates these series of functions.

As soon as this aperture 3 has moved in the direction of the arrow over the width of the sector S12, the beams originating from the collimator 2 are modulated by the next function. In each position of the body 4 in FIG. 1, the aperture 3 must only be rotated so far that all functions are present in front of the collimator one time, i.e. through the angle which covers a complete function on the circumference (at the most 360°).

The boundaries of the sectors situated at the ends of the collimator 2 (in the position shown by the boundaries of the sector S14) in FIG. 3 do not extend perpendicularly to the direction of the collimator; however, this results in only a minor deviation of the values thus obtained. This deviation, however, is smaller than the aperture, (or the ratio between the distance from the collimator to the point of rotation of the aperture 3 and the length of the collimator 2, is larger) so that a complete function occupies a small angular region on the aperture 3 and a correspondingly larger number of functions can be arranged on the circumference. A further deviation of the values arises if the aperture 3 is continuously moved and, a smooth transition takes place from the one function to the next function. This provides a kind of "cross talk" between adjacent radiation beams and hence between adjacent intensity values. It has the same effect as if the spatial detection regions of the individual detectors overlap in the known application of separate detector elements per radiation beam. This effect is very desirable, because it reduces so-termed aliasing, (folding back of high spatial frequency regions into lower frequency regions which is caused by details which are smaller than the diameter of a radiation beam).

It is to be noted that the apertures may also have other shapes, for example, they may be tubular, the radiation source 1 and the collimator 2 are then inside the tube.

When the described device is used in an X-ray system for medical purposes, a minimum radiation dose is desirable. The lower limit of the radiation dose is determined so that the signals generated by the radiation detector element 6 are large with respect to the noise generated by the detector element and the amplifier. It has been found that the visual impression of the image does not deteriorate when the higher frequencies of the absorption function contain more noise. The overall radiation dose is also determined by the period of time during which the aperture 3 transmits the individual radiation beams, thus the apertures sectors of the aperture shown in FIG. 2 may be chosen to be smaller in the aperture area which generates the higher sequences of the intensity function. Said sectors preferably start later in the direction of rotation of the aperture. Alternately bridges can also be situated in the sectors at the edges of the radiation beams associated with these functions for the higher sequences. The bridges can be widened or the attenuation factor of the aperture area can be increased when use is made of functions other than the Walsh functions. The effect of the described step for reducing the radiation dose is in any case such as if the radiation beams for the higher sequences are modulated by an amplitude which is correspondingly smaller than the value which corresponds to the function value of the associated function; This reduction of the amplitude must be taken into account for the processing of the discrete signal values derived from the detector signal. This possibility for reducing the radiation dose, however, exists only when use is made of function systems which generate the coefficients of the individual sequences, that is to say notably for Walsh functions, but not for the described m functions.

A further reduction of the radiation dose used for measuring the absorption values can be realized if the function in the function system or the associated aperture section which supplies the mean value of the absorption values, (that is to say the sum of the intensities of all radiation beams) is omitted. In the embodiment of an aperture as shown in FIG. 2, the sector S1 could then be non-transmissive, and the processing device 8 in FIG. 1 would derive only three function values from the output signal of the detector 6 or the amplifier 7. An arbitrary function value may be chosen for the mean value (or equivalent value) (for example, it may also have the value zero), but it has been found that this arbitrary function value is preferably chosen so that the back-transformed values are all positive prior to logarithmation in the device 8. On the other hand, this in order to avoid the processing of unnecessary large numbers during the further processing of the back-transformed values this arbitrary value should not be too large.

After determination of the absorption values of the body 4 in different measuring positions of the body 4 in the same plane, with respect to the device the two-dimensional absorption distribution of the body can be calculated. However, the absorption distribution in various successive planes of the body is often of interest. This can be achieved by displacement of the body perpendicularly to the plane of the drawing in FIG. 1 after each series of measurements. Instead, by choosing a corresponding shape of the collimator 2, a two-dimensional fan of radiation beams 5 can be generated in the form of a number of flat fans of radiation beams, which are situated one behind the other, so that the absorption distribution in different planes of the body can be simultaneously determined. In the device shown in FIG. 1, several detector devices 6 are then arranged on behind the other, each detector device comprising its own amplifier 7 and its own, separate processing device 8. The intensities and hence the absorption values are thus simultaneously generated for radiation beams situated one behind the other. If the processing speed of the processing device 8 is high enough, it can also be used for all detector elements 6. Signals are processed in time multiplex. This is particularly advantageous for the aperture shown in FIG. 2, several slit-shaped collimators 2 then being arranged one above the other behind the aperture. Rotation of the aperture causes the sector ends to block the radiation beams from the various collimators for the various planes of examination at different instants. In order to block the radiation beams from a collimator or a plane as much as possible at the same instant, it is more attractive to select a larger aperture and to select a larger ratio of the inner radius with respect to the outer radius of the sectors (nearer to 1). In principle, the aperture shown in FIG. 2 can also be used for the case involving the two-dimensional fan of radiation beams. The aperture shown in FIG. 3 can also be used, if the individual sectors have sufficient length in the radial direction to cover several slit-shaped collimators.

Figure 4:
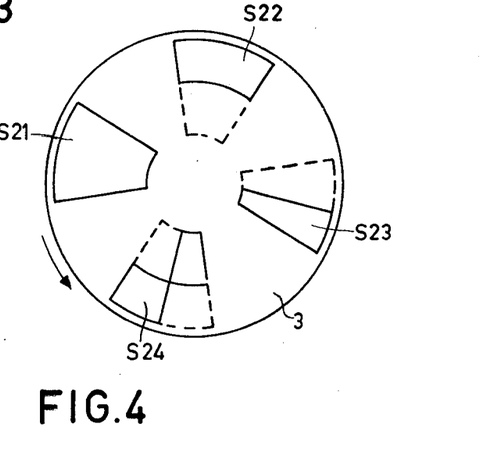
FIG. 4 shows an embodiment of an aperture for a two-dimensional Walsh-Hadamard function system, FIG. 5 diagrammatically shows a further device in accordance with the invention.

A single detector element can also be used for the entire two-dimensional fan of radiation. Only one amplifier 7 and one processing device 8 are present. In this case the two-dimensional fan of radiation beams 5 must be modulated by the functions of a two-dimensional, complete, linearly-independent function system and the processing device 8 must perform a two-dimensional inverse transformation of the discrete signal values. FIG. 4 shows an example of an aperture 3 with a two-dimensional Walsh function. Therein, the sector S21 is fully transmissive. Only the upper half of the sector S22 is fully transmissive, whilst the lower half (denoted by broken lines) is not transmissive. Only one half of the sector S23 is transmissive. The separating line, however, now extend in the radial direction. The transmissive and non-transmissive parts of the sector S24 are arranged in a checkboard pattern.

When use is made of such an aperture the four signal values successively derived from the detector 6 are multiplied by values in a manner which corresponds to the two-sided matrix multiplication:

$$[B], = C \begin{pmatrix} 1 & 1 \\ 1 & -1 \end{pmatrix} [b] \begin{pmatrix} 1 & 1 \\ 1 & -1 \end{pmatrix}$$

To achieve the inverse transformation B is the image matrix (i.e. the two-dimensional distribution of the intensity values for non-modulated radiation, b is the transformed matrix which results from the values which are arranged matrix-wise and which are successively derived from the detector element, and C is a standardization factor. Generally, if the transformed matrix is dependent on the image matrix as follows by modulation by means of correspondingly formed apertures:

$$[b] = [T] \cdot [B] \cdot [T]^+,$$

where T and $T^+$ are matrices inverted with respect to each other which determine the modulating functions, the inverse transformation is derived therefrom as follows:

$$[B] = [T]^+ \cdot [b] \cdot [T]$$

If a separable transformation is used, the rows can be successively transformed by matrix multiplication at the left-hand side and the columns by matrix multiplication at the right-hand side. In the case of non-separable function systems, a tensor operation of higher order must be executed; this is also possible for separable systems but requires more calculations.

The steps for reducing the radiation dose by omission of the equivalent and the reduction of the amplitude of the sequences of higher order can in principle also be used for two-dimensional function systems if these systems produce a transformation in the applicable sequence range.

In the embodiment shown in FIG. 1, the aperture 3 is arranged between the radiation source 1 and the body 4 to be examined. However, the aperture 3 can in principle also be arranged between the body 4 and the detector device 6. This is shown in FIG. 5, in which the elements corresponding to FIG. 1 are denoted by corresponding reference numerals.

The radiation beams 5 having passed through the body first reach an image conversion tube 11 which, with high sensitivity, converts the radiation emitted by the radiation source 1 (which may again be an X-ray tube) into visible light. The information carried by the radiation is not modified; only its representation is changed.

Figure 5:
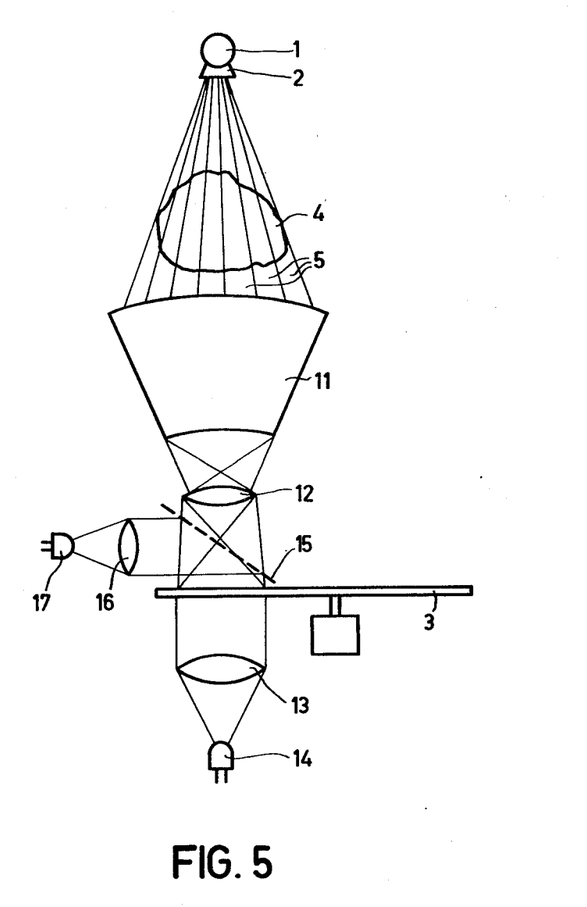

The visible light emitted by the conversion tube 11 is imaged, by an optical system 12, onto the rotating aperture 3, which may be constructed similar to the embodiments shown in the FIGS. 3 to 5. The radiation transmitted by the aperture 3 is collected on a detector element 14 by an optical system 13. The element may, for example, be a photodiode. The signal from the photodiode 14 is treated in the same manner as the signal from the detector device 6 in FIG. 1.

In this case only a part of the radiation having passed through the body 4 is used, via the aperture 3, by the photodiode 14, the body 4 is exposed to a correspondingly larger radiation dose. In order to utilize also the radiation which is not transmitted by the aperture 3, the side of this aperture which faces the optical system 12 is made to be reflective and a semi-transparent mirror 15 is arranged between the aperture 3 and the optical system 12. As a result, the radiation which is not transmitted by the aperture 3 is reflected, deflected by the mirror 15 and collected on a second photodiode 17 by the optical system 16. The two photodiodes 14 and 17 thus supply signals which are complementary with respect to each other. In the case of Walsh functions, for example, the value "1" can be assigned to the photodiode 14 and the value "−1" to the photo diode 17, with the result that the electrical signals from the photodiodes 14 and 17 can be subtracted from each other in order to determine the ultimate electrical signal.

Figure 6:
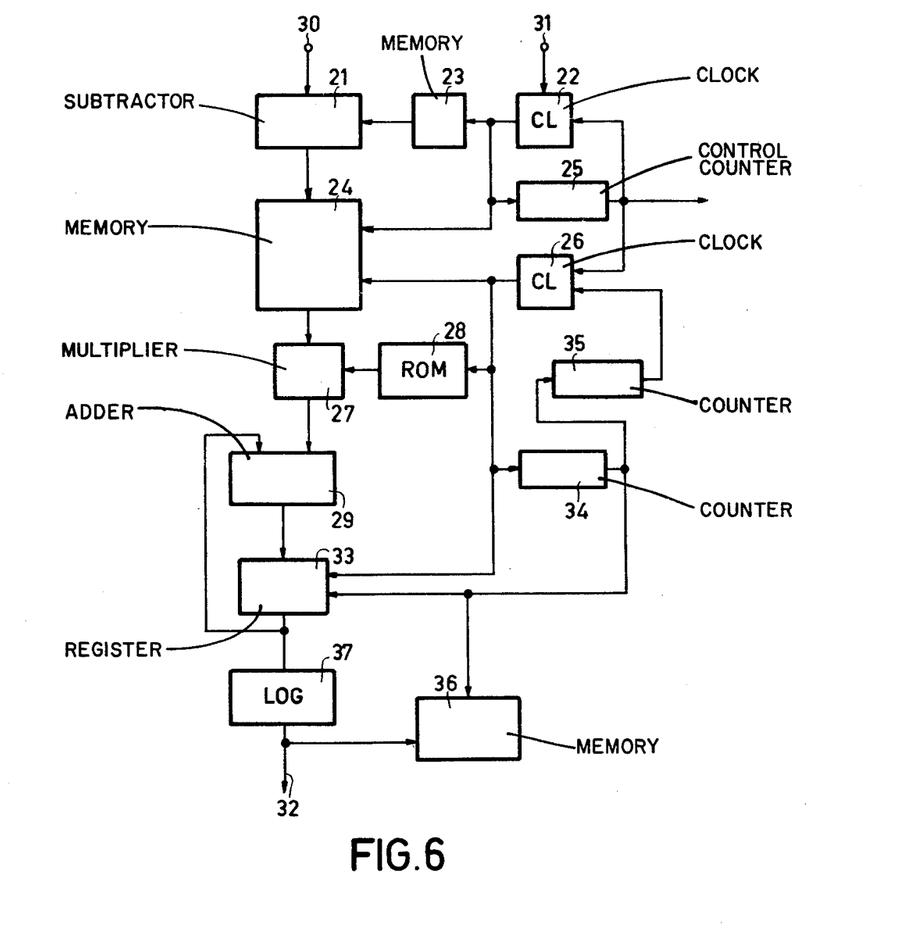
FIG. 6 shows a block diagram of the processing device associated with the device in accordance with the invention as shown in FIGS. 1 and 5.

FIG. 6 shows an embodiment of the processing device 8 shown in FIG. 1. When use is made of "shifted" functions during modulation, as for Walsh functions described with reference to FIG. 2, the signals supplied by the amplifier 7 in FIG. 1 are applied, via the input 30, to a subtraction stage 21 which subtracts a signal value measured first and stored in the memory 23, from the signal values. The non-modified spectral Walsh values of the intensity function thus obtained are written in a memory 24, the write operation being controlled by the clock of a clock generator 22.

The clock generator 22 is triggered by a synchronization signal which is applied to the input 31 and which can be generated in known manner in dependence of the rotation of the aperture 3, for example, photoelectricly or magneticly) at the instant at which, for the aperture shown in FIG. 2, the end of the sector 1 has reached its position in front of the collimator 2. Alternatively, a signal can be generated at the end of each sector so that the clock 22 need not be a self-exciting oscillator, but only an amplifier. In the other case the clock generator automatically generates pulses at intervals which correspond to the passage of the individual sectors of the aperture in front of the collimator.

The memory 24 may be a random access memory, a silo memory or a shift register. The clock 22 supplies clock pulses to a first control counter 25 which, after having counted the predetermined number of clock signals and hence signal values, supplies an output signal on the output 30 which corresponds to the number of different functions or aperture sectors. The output signal blocks the clock 22 and triggers a further clock 26. At the same time, the output signal causes rotation of the body 4 in FIG. 1 with respect to the measuring device in order to adjust the next measuring position. During this adjusting time, the synchronization signals are suppressed by the aperture 3.

During this period, the clock 26 supplies clock signals which successively read the signal values previously stored in the memory 24 in the same sequence and which apply these values to a multiplier 27. At the same time, these clock signals control a read-only memory 28 which successively supplies the values of the inverse-transformation matrix line-wise. When Walsh function are used for the modulation in the described manner, this inverse-transformation matrix only contains the values 1 or −1, and the multiplier 27 only has to reverse the sign.

The output values of the multiplier 27 are applied to a first input of an adder 29, the output of which is connected to a register 33. The output of the register connected to the second input of the adder 29. The adder 29 cooperates with the register 33 to act as an accumulator. If the adder 29 comprises a control input for switching over to subtraction, it is advantageous, when Walsh functions are used for modulation, to control this control input directly from the output of the memory 18. The multiplier 27 can thus be omitted.

The clock signals generated by the clock generator 26 write the previously processed value into the register 33 in reaction to each reading of the next value from the memory 27. A counter 34 is advanced by one position. After having counted a number of clock signals which corresponds to the number of functions used for the modulation, counter 34 supplies an output signal which indicates that the content of the register 33 represents an inverse-transformed intensity value of a radiation beam. The absorption value is obtained from this intensity value known manner by taking the logarithm in the stage 37. This absorption value is output via the output 32 and is applied to a device for the reconstruction of the two-dimensional absorption distribution. Instead, this register content can also be written in a further memory 36 which stores all absorption values of the complete series of measuring positions and which at a later stage outputs these data for determining the absorption distribution in the plane. Subsequently, the register 33 is erased by this output signal in order to enable determination of the next back-transformed intensity value or absorption value.

The values present in the memory 24 are read again using the next clock pulses from the clock generator 26, so that this memory must be suitable for non-destructive reading. At the same time, the signal values of the next line of the back transformation matrix are read from the memory 28. When the next output signal of the counter 34 appears accumulating addition ultimately produces the next inverse-transformed intensity value in the register 33 and the next absorption value on the output 32.

Thus, all absorption values of the body 4 along the individual radiation beams are successively recovered and the number thereof is equal to the number of functions of the function system used for modulation. Therefore, the output signal of the counter 34 is applied to a further counter 35 which also supplies an output signal when a position is reached which corresponds to the number of functions. The output signal stops the clock generator 26 because the inverse transformation has been terminated. The synchronization signal is released again by the aperture as soon as the body 4 in FIG. 1 has reached the new measuring position with respect to the measuring device, the next series of signal values corresponding to the transformed intensity series then appears on the output 30 and is step-wise written in the memory 24. The inverse transformation of the values present memory 24 must, therefore, be terminated in the until the body 4 has reached its new measuring position and the frequency of the clock generator 26 must be chosen accordingly.

What is claimed is:

1. In a device for determining the absorption distribution in a body; of the type comprising substantially point-shaped source means which generate radiation in separate beams which penetrate the body, detector means which measure the radiation from the source means which penetrates the body and generate detector signals therefrom, and processing means which derive electrical signals which are representative of the absorption of the body along the radiation beams from the detector signals, the improvement wherein:

the detector means comprise one or more detector elements each of which measures radiation in a group of adjacently situated radiation beams;

the device further comprises modulation means which modulate the intensity of radiation in the beams with time varying functions, each of the beams measured by an individual detector element being modulated by a separate function which is linearly independent of the functions which modulate other beams measured by that detector element; and the processing means derives individual signals which correspond to the intensity in each of the radiation beams in a group from the output of the associated detector element by multiplying discrete signal values received from the detector element by a matrix of values which is the inverse of the functions used to modulate the beams in the group.

2. An improved device as claimed 1 wherein the modulation means functions to modulate each beam with a number of discrete function values during predetermined periods of time, the number of discrete function values being equal to the number of modulating functions.

3. An improved device as claimed in claim 2 wherein the modulation means functions to modulate some beams in the group with higher sequence functions and other beams in the group with lower sequence functions, the beams associated with the lower sequence functions being modulated for a longer period of time than the beams associated with the higher sequence functions, the beams associated with higher sequence functions being blocked during the remaining modulation time of the lower sequence beams.

4. An improved device as claimed in claims 1, 2 or 3 wherein the modulation means function to eliminate a mean value from the modulation functions which are applied to the beams.

5. An improved device as claimed in claim 4 wherein the radiation beams, are disposed as a two-dimensional fan and wherein the detector means comprise a plurality of detector elements, each detector element being disposed to receive radiation from the group of all adjacent beams along a single dimension of the fan.

6. An improved device as claimed in claim 4 wherein the radiation beams are disposed as a two-dimensional fan, wherein a single detector element measures all radiation in the fan, and wherein the modulation means operates to modulate the radiation beams with functions which form a two-dimensional, linearly independent function system.

7. An improved device as claimed in claim 4 wherein the modulation means comprises a moveable aperture which includes radiation transmissive zones and radiation non-transmissive zones which are distributed in accordance with the modulated functions, the aperture being disposed between the radiation source means and the detector means.

8. A device as claimed in claim 7 wherein the aperture comprises one or more rotating discs.

9. An improved device as claimed in claims 1, 2 or 3 comprising one detector element which measures all of the radiation beams.

10. An improved device as claimed in claim 9 wherein the radiation beams are disposed as a two-dimensional fan and wherein the detector means comprise a plurality of detector elements, each detector element being disposed to receive radiation from the group of all adjacent beams along a single dimension of the fan.

11. An improved device as claimed in claim 9 wherein the radiation beams are disposed as a two-dimensional fan, wherein a single detector element measures all radiation in the fan, and wherein the modulation means operates to modulate the radiation beams with functions which form a two-dimensional linearly independent function system.

12. An improved device as claimed in claim 9 wherein the modulation means comprises a moveable aperture which includes radiation transmissive zones and radiation non-transmissive zones which are distributed in accordance with the modulating functions, the aperture being disposed between the radiation source means and the detector means.

13. A device as claimed in claim 12 wherein the aperture comprises one or more rotating discs.

14. An improved device as claimed in 1, 2 or 3 wherein the radiation beams are disposed as a two-dimensional fan and the detector means comprise a plurality of detector elements, each detector element being disposed to receive radiation from the group of all adjacent beams along a single dimension of the fan.

15. An improved device as claimed in claim 1, 2 or 3 wherein the radiation beams are disposed as a two-dimensional fan, wherein a single detector element measures all radiation in the fan, and wherein the modulation means operates to modulate the radiation beams with functions which form a two-dimensional, linearly independent function system.

16. An improved device as claimed in claim 15 wherein the modulation means comprises a moveable aperture which includes radiation transmissive zones and radiation non-transmissive zones which are distributed in accordance with the modulating functions, the aperture being disposed between the radiation source and the detector means.

17. A device as claimed in claim 16 wherein the aperture comprises one or more rotating discs.

18. An improved device as claimed in claim 1, 2 or 3 wherein the modulation means comprises a moveable aperture which includes radiation transmissive zones and radiation non-transmissive zones which are distributed in accordance with the modulating functions, the aperture being disposed between the radiation source means and the detector means.

19. A device as claimed in claim 18 wherein the aperture comprises one or more rotating discs.

* * * * *